United States Patent
Fogarty et al.

(10) Patent No.: US 6,168,623 B1
(45) Date of Patent: Jan. 2, 2001

(54) DEFORMABLE CONDUITS AND METHODS FOR SHUNTING BODILY FLUID DURING SURGERY

(75) Inventors: Thomas J. Fogarty, Portola Valley; Timothy J. Ryan, Menlo Park, both of CA (US)

(73) Assignee: Cardiothoracic Systems, Inc., Cupertino, CA (US)

(*) Notice: Under 35 U.S.C. 154(b), the term of this patent shall be extended for 0 days.

(21) Appl. No.: 09/143,995

(22) Filed: Aug. 31, 1998

(51) Int. Cl.⁷ ........................................... A61F 2/00
(52) U.S. Cl. ..................... 623/1.3; 623/1.1; 623/1.37; 623/23.64
(58) Field of Search .................. 623/1.11, 1.25, 623/1.27, 1.3, 1.31, 1.32, 1.44, 1.49, 1.5, 1.51, 1.37, 23.64

(56) References Cited

U.S. PATENT DOCUMENTS

| | | | |
|---|---|---|---|
| 3,435,824 | 4/1969 | Gamponia | 128/334 |
| 3,991,767 | 11/1976 | Miller, Jr. et al. | 128/348 |
| 4,130,904 | * 12/1978 | Whalen | 623/1.44 |
| 4,712,551 | 12/1987 | Rayhanabad | 128/334 |
| 4,721,109 | 1/1988 | Healey | 128/334 |
| 4,753,736 | 6/1988 | Reichgott | 210/674 |
| 5,129,883 | 7/1992 | Black | 604/101 |
| 5,151,105 | * 9/1992 | Kwan-Gett | 623/1.32 |
| 5,234,425 | 8/1993 | Fogarty et al. | 606/1 |
| 5,443,499 | * 8/1995 | Schmitt | 623/1.49 |
| 5,453,084 | 9/1995 | Moses | 604/8 |
| 5,456,721 | * 10/1995 | Legrand | 623/1.5 |
| 5,476,506 | * 12/1995 | Lunn | 623/1.31 |
| 5,562,727 | * 10/1996 | Turk et al. | 623/1.44 |
| 5,713,948 | * 2/1998 | Uflacker | 623/12 |
| 5,782,904 | * 7/1998 | White et al. | 623/1.32 |
| 5,876,448 | * 3/1999 | Thompson et al. | 623/12 |
| 5,904,714 | * 5/1999 | Nunez et al. | 623/1 |

* cited by examiner

*Primary Examiner*—Michael J. Milano
(74) *Attorney, Agent, or Firm*—Limbach & Limbach LLP

(57) ABSTRACT

The present invention comprises a tubular shunt for insertion into a fluid vessel in a living creature constructed of an elastically deformable material that reduces in circumference when stretched longitudinally so that the ends of the shunt may be easily inserted into openings in a blood vessel and where the material expands circumferentially when allowed to axially contract such that the ends of shunt press against the vessel wall to secure the shunt and form a water tight seal to permit fluid to flow through the tubular conduit of the shunt. A method for shunting fluid-flow in a portion of a vessel in a living creature is also disclosed wherein a shunt of the present invention is stretched longitudinally so that the ends of the shunt contract and then inserted into a lumen of a blood vessel. Following insertion of the shunt, the shunt is allowed to return to its relaxed geometry so that it forms a fluid tight seal with the interior of the lumen.

32 Claims, 15 Drawing Sheets

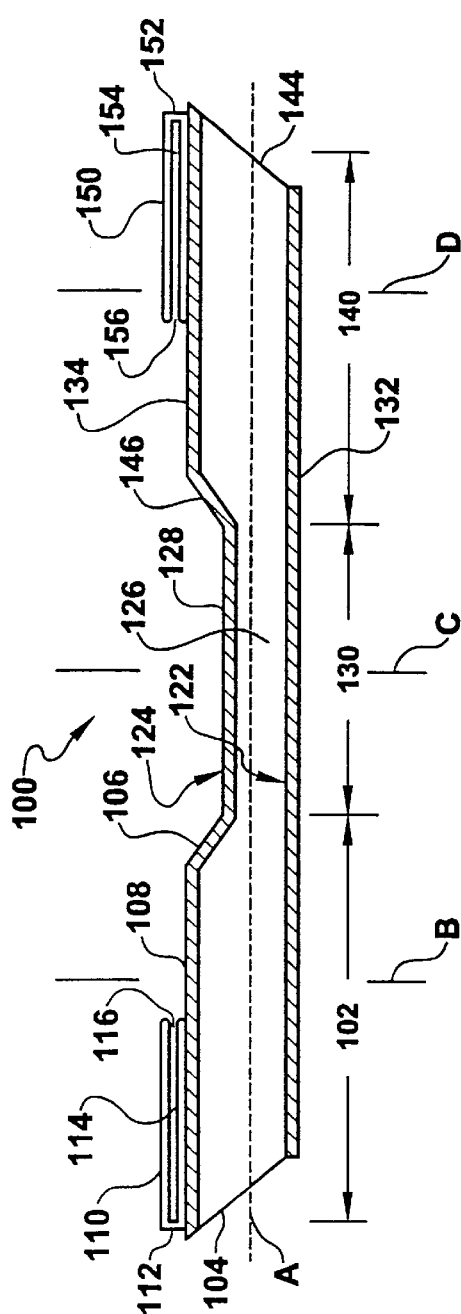
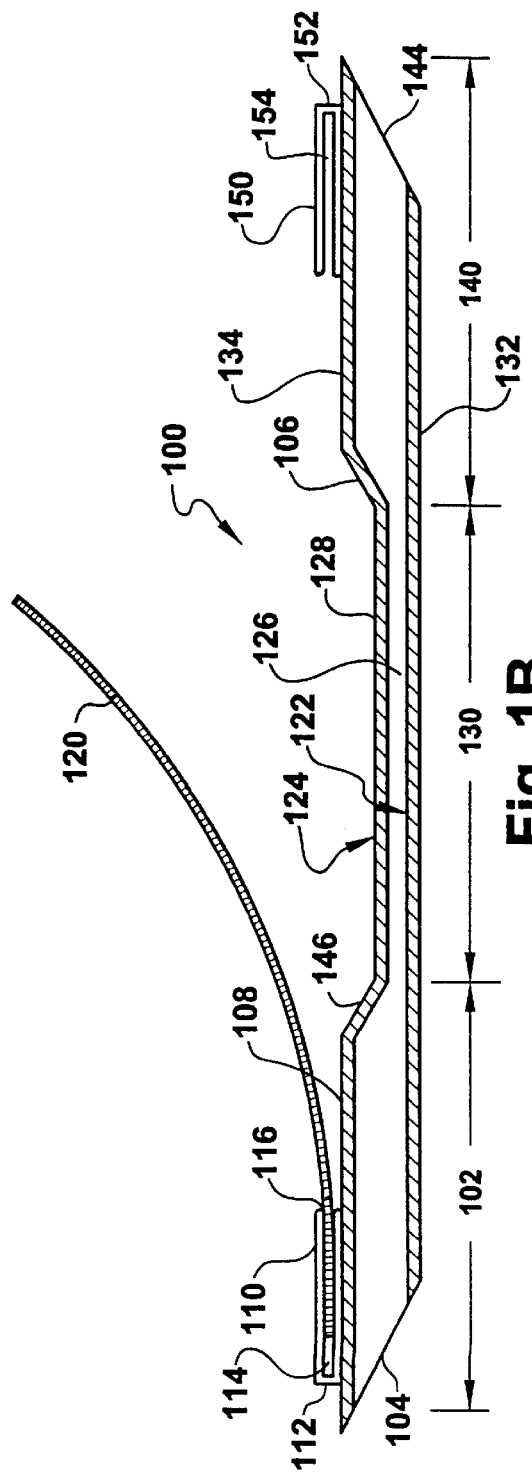
Fig. 1A
Fig. 1B

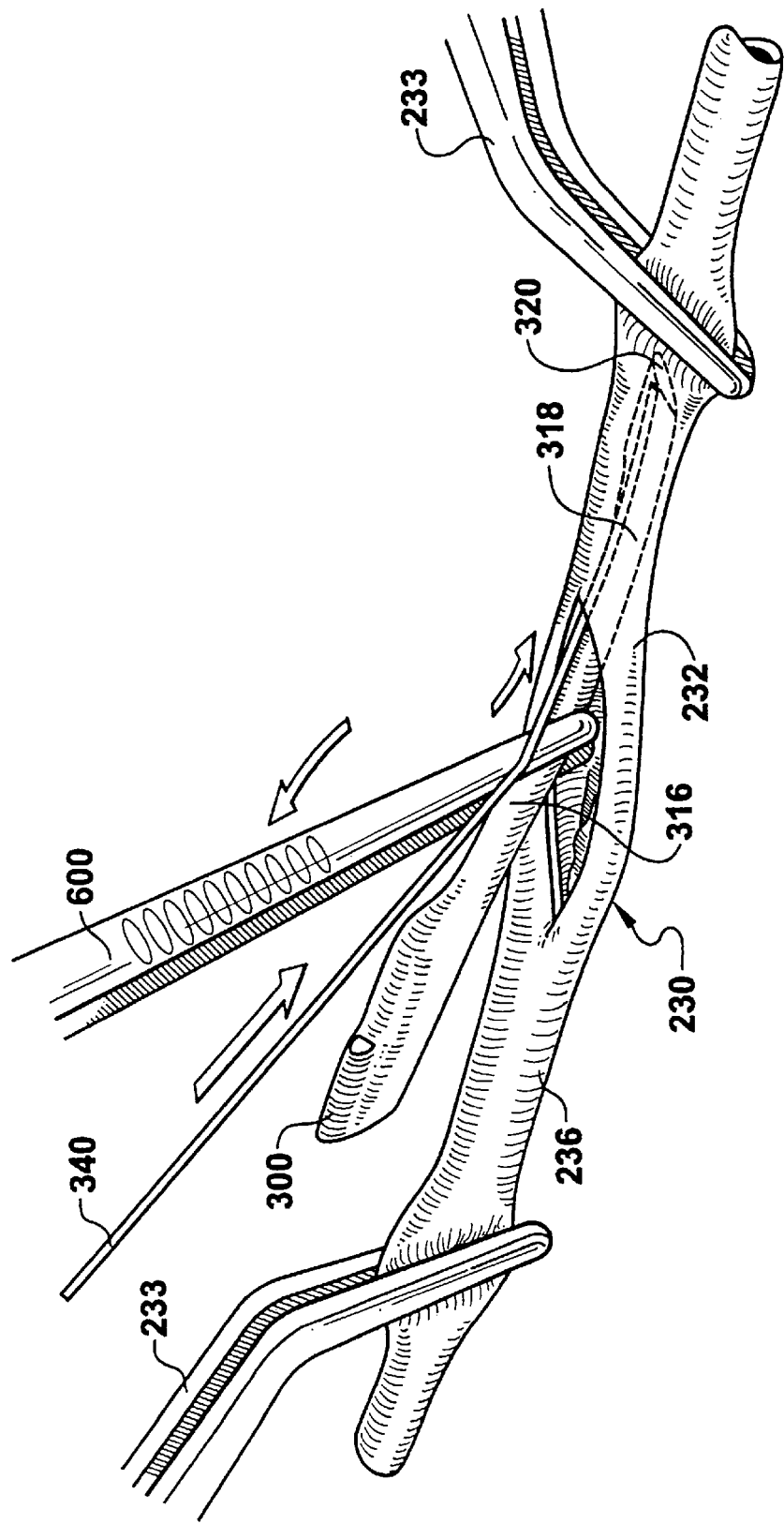

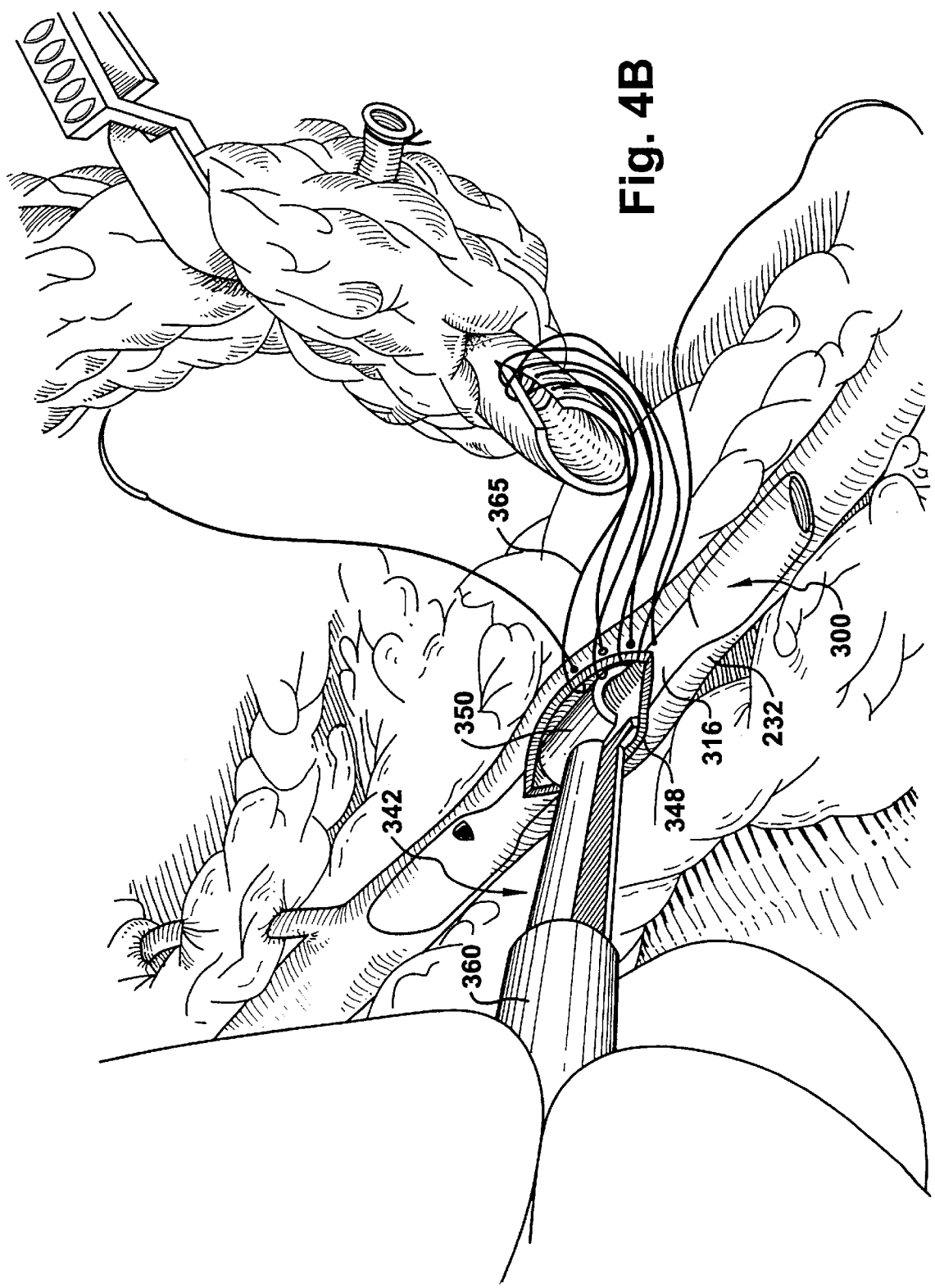

DEFORMABLE CONDUITS AND METHODS FOR SHUNTING BODILY FLUID DURING SURGERY

FIELD OF THE INVENTION

The invention relates generally to prosthetic conduits or shunts used in surgery to bypass or reroute the flow of a bodily fluid. More particularly, the invention relates to conduits or shunts which are used temporarily during surgery to allow an uninterrupted flow of blood to tissues whose normal blood supply has been at least partially interrupted by a surgical procedure on a vessel such as an artery. These conduits are frequently used during procedures in which the affected tissue is particularly sensitive to a decreased blood supply. Examples of procedures in which sensitive tissues may benefit from an uninterrupted blood supply include carotid endarterectomy, coronary artery bypass grafting on an arrested, partially arrested or beating heart, and thoracoabdominal aortic reconstructions. The use of a shunt during each of these procedures protects the brain, the myocardium, and the spinal cord, respectively.

BACKGROUND OF THE INVENTION

Many different vascular shunts or catheters are currently employed during surgery to maintain blood flow in extremities and tissues served by a blood vessel undergoing a surgical procedure. One example, the Pruitt-Inahara carotid shunt (described in U.S. Pat. No. 3,435,824), includes the use of a tube having inflatable bladders encircling each end of the tube and further includes a duct for the passage of blood. During the surgical procedure, the vessel undergoing the procedure is partially cut through and the ends of the tube inserted into the vessel. The bladders are then inflated to a pressure that causes the ends of the tube to be retained within the vessel but without causing the vessel wall to overextend and rupture due to overinflation of the bladders. Care must be taken to monitor the pressure in the bladders during inflation to limit damage to the vessel though some damage to the endothelium is common. A central portion of the shunt between the ends remains outside the vessel and is commonly looped in a circular manner to prevent crimping of the plastic or silicone rubber tubing which forms the central portion of the shunt. Upon completion of the surgical procedure, the incisions around the ends of the shunt are loosely sutured, the bladders are deflated to permit the ends of the shunt to be withdrawn from the vessel, and the sutures are pulled tight to close the incisions.

Moses, U.S. Pat. No. 5,453,084, describes another example of a vascular shunt wherein a tube is inserted into the incised vessel and a ring clamp or purse suture is applied to the vessel wall at the position of each end of the tube to create a water seal between the vessel wall and the shunt tube and to hold the ends in place within the vessel. The tube is fabricated of a transparent material to permit observation of the fluid flowing through the shunt in order to verify that the shunt is functioning. In addition, the tubing material must be flexible enough to permit the tube to be manipulated into position but must also resist crimping so as not to occlude the flow of fluid through the shunt when it is bent. The shunt is removed by removing the ring clamps or loosening the purse sutures holding the shunt in place, withdrawing the shunt through the open incisions. The sutures are then tightened to close the incisions. The use of clamps or sutures to hold the shunt in place can cause neuro-muscular trauma to the vessel in the regions of contact.

Black, U.S. Pat. No. 5,129,883, describes a catheter adapted to be inserted into a patient's circulatory system and threaded through to a portion of the system to be shunted. The catheter includes inflatable cuffs with a conduit that permits blood flow to bypass the region of the vessel between the cuffs. When the cuffs are inflated, blood flow is diverted through the conduit. As with the Pruitt-Inahara shunt above, the inflation pressure in the cuffs must be monitored to limit the amount of damage done to the vessel wall by the inflatable cuffs. Rayhanabad (U.S. Pat. No. 4,712,551) and Miller, Jr. et al. (U.S. Pat. No. 3,991,767) each describe variations on a tubular shunt with an inflatable cuff.

Healey, U.S. Pat. No. 4,721,109 describes a single piece device with a center tube and inflatable outer casing wherein the center tube fits into the ends of a damaged blood vessel to reconnect the two ends and conduct blood and the inflatable outer casing expands to secure the device within the vessel. Healey (U.S. Pat. No. 4,753,236) also describes a two piece device wherein each piece has an inflatable outer casing and a tubular internal portion wherein the two tubular portions include connectors adapted to couple to one another. The inflatable casings expand to secure each piece into an opening in a severed vessel and the tubular portions are coupled together to reconnect the ends of the vessel.

SUMMARY OF THE INVENTION

It is an object of the present invention to provide methods and devices for temporarily shunting a fluid-carrying vessel or tubular tissue structure in a living creature to provide uninterrupted flow of fluid through the vessel or tissue structure during a surgical procedure.

Another object of the present invention is to provide a shunt apparatus positionable within an incision in a blood vessel such that the shunt provides a substantially bloodless field around the incision site.

Another object of the present invention is to provide a shunt apparatus having a tubular structure constructed of an elastically deformable material that reduces circumferentially when axially lengthened and expands circumferentially toward an original, biased circumference when allowed to axially contract.

Another object of the present invention is that the circumference of the ends of the shunt apparatus will expand when the ends are released such that the ends securely lodge against the inner walls of a vessel into which the shunt is inserted and hold the shunt apparatus in place within the vessel lumen.

Yet another object of the present invention is that the circumference of the ends of the shunt apparatus may be reduced for easy insertion into the openings of an incised vessel.

It is a further object of the present invention that the shunt be secured within the vessel without the use of clamps or inflatable bladders.

It is an additional object of the present invention that the shunt apparatus may be easily repositioned within the vessel without interrupting the flow of fluid through the shunt apparatus.

Accordingly, the present invention provides a shunting device for implantation in a fluid-carrying vessel or tubular tissue structure having an elastically deformable, generally tubular body structure. The body structure has contiguous segments or regions including first and second end portions and a central region therebetween to collectively define a conduit having a longitudinal axis. Stretching at least one end portion of the shunting device along the longitudinal axis results in a reduction in a dimension of the tubular structure which is transverse to the longitudinal axis. The shunting device further includes means associated with the tubular body for facilitating the insertion and positioning of the shunting device within a vessel or tubular tissue structure. Such a means may include a receptacle integrally formed in the tubular body structure to receive a free-standing positioning stylus. Alternately, the means may include a stylus attached to one or both of the end portions of the tubular body with or without a positioning tube.

More particularly, the apparatus of the present invention includes a composite tube with a relatively large, relaxed circumference at both ends, and a smaller circumference section in the middle. The tube is constructed such that elongating the tube causes the circumference to reduce by about half. In a first embodiment, the tube is constructed of a tubular braided monofilament, which is then impregnated with an elastomeric material to provide vessel sealing and elasticity. Further, the larger circumference segments taper down to the smaller center segment, and the smaller circumference segment is substantially aligned with the outer aspect of the two larger circumference segments. Preferably, each of the ends of the tube is cut at an oblique angle.

Positioned on the outer surface along each the larger circumference segments of the tube is a closed-end positioning receptacle or cavity into which a stylus, such as a pushrod or wire, may be inserted to elongate the tube. This receptacle may extend partially along the larger circumference segment or back and over to the smaller circumference segment. The receptacle or cavity may be positioned on the outside surface of the main shunt tube, or it may be positioned along the inside surface of the tube at the ends and pass through the wall of the tube to the outer surface somewhere along the length of the tube. Ideally, this receptacle is sufficiently flexible that it collapses at least partially when the push rod is removed. This push rod receptacle may be fixed to the wall of the main shunt tube at the ends only or it may be fixed to the wall along the entire length. An advantage of extending the outer tube to the mid section of the shunt is that the shunt may be repositioned without removing the shunt from the vessel.

In another embodiment of the present invention, the shunt may have a thin stylus, such as a fine-gauge wire, attached to the tip of the obliquely cut end and extending back to at least the central portion of the shunt. The stylus may be used independently to stretch the shunt or may be used in conjunction with a narrow-lumen positioning sleeve, preferably made of metal or plastic. The position sleeve is passed over the wire to the end of the shunt while pulling on the wire to selectively extend the shunt. The pressure that the sleeve exerts against the end of the shunt causes elongation of the shunt which collapses the tube for easy insertion into a vessel.

In another embodiment, the wire stylus may have a sharpened distal end. In use, the sharpened end of the stylus is used to penetrate the outer surface of the end portion of the shunt. The stylus is then used to stretch the shunt so as to decrease the diameter of the shunt for insertion into the vessel. The shunt is preferably configured from a soft silicone or elastomer which allows penetration by the sharpened stylet without compromising the integrity of the blood lumen of the shunt.

In another embodiment of the present invention, a shunt positioning tool configured to securely hold and manipulate the shunt is provided. The positioning tool comprises a first and second elongate arm members which may be biased from an open to a closed position so as to securely engage a shunt between first and second semi-cylindrical distal ends of the arms. The shunt positioning tool may include a locking ring which is operable to securely fix the distal ends about the shunt during insertion or manipulation of the shunt. A pair of wire guides may also be included to accurately guide the distal movement of one or more stylets so as to stretch and contract the shunt for installation or manipulation of the shunt.

These and other objects, features and advantages will become apparent when considered with reference to the following description and the accompanying drawings.

BRIEF DESCRIPTION OF THE DRAWINGS

FIG. 1A is an axial cross-sectional diagram of an embodiment of a shunt apparatus of the present invention in its natural or unstretched condition.

FIG. 1B is an axial cross-sectional diagram of the embodiment of FIG. 1A in a stretched or lengthened condition and an embodiment of a stylus of the present invention functionally positioned within a positioning receptacle of the shunt apparatus.

FIG. 4A is a diagram showing the stretched end of the shunt apparatus of FIGS. 1A and 1B being inserted into the vessel lumen of the vessel of FIG. 2.

FIG. 4B is a shunt positioning tool of the present invention shown manipulating a shunt device in a target coronary artery of an anastomosis with the left internal mammary artery.

DETAILED DESCRIPTION OF THE PREFERRED EMBODIMENTS

Figure 2:
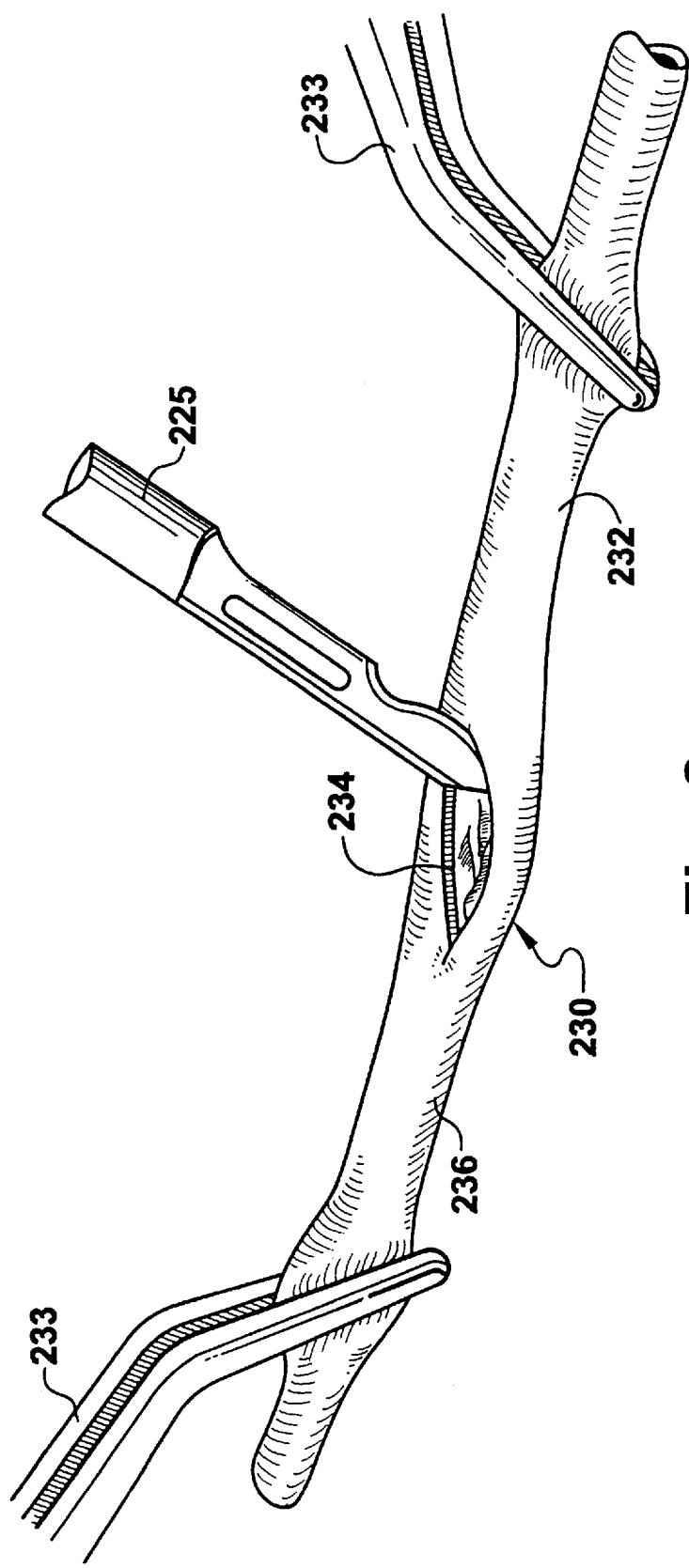
FIG. 2 is a diagram showing a vessel being incised to permit insertion of a shunt apparatus of the present invention.

Turning now to the drawings where like reference numbers refer to like elements of the invention, there are shown various embodiments of the shunt apparatus of the present invention. FIGS. 1A and 1B are cross-sectional side views illustrating one embodiment of the shunt apparatus 100 of the present invention in its natural (i.e., unstretched) and lengthened (i.e., stretched) conditions, respectively. Shunt apparatus 100 consists of a continuous tube body 108 defining a longitudinal axis A and having an inner surface 122 and outer surface 124 defining a fluid conduit or lumen 126. Tube 108 has various contiguous portions or segments, namely, two end portions or segments 102 and 140 and a central portion or segment 130 therebetween. End regions 102 and 140 terminate in tips 104 and 144, respectively, which preferably have a tapered, pointed, or oblique design to facilitate insertion of shunt 100 into a vessel or tissue structure.

From the cross-sectional side view of FIG. 1A, tube 108 can be described as having lower and upper wall portions 132 and 134 about axis A. Lower wall portion 132 is preferably substantially linear for the entire length of the tube so that, when implanted or positioned within a fluid-carrying vessel or tissue structure, lower wall portion 132 fits flush against at least a portion of the inner wall of the vessel or tissue structure. Upper wall portion 134 has tapered areas 106 and 146 which define the inner portions of regions 102 and 140, respectively, and which, in the view of FIG. 1A, defines a recessed area 128 of central segment 130. As such, the respective dimensions transverse to axis A (e.g., inner and outer diameters and circumferences) of tube 108 at end segments 102, 140, identified generally about axes B and D, are greater than at central segment 130, identified generally about axis C. Upon insertion through an incision made in a vessel or the like, recessed area 128 is generally positioned to face outward through the incision to provide a working space within the vessel while minimizing the escape or leakage of blood or other fluid at the surgical site. The working space may facilitate, for example, the removal of plaque in an endarterectomy procedure performed on the vessel or the forming of an anastomosis in a coronary artery bypass graft procedure.

Tube body 108 is preferably constructed of a biologically compatible, elastic material that is deformable to be generally conformable, particularly at end regions 102 and 140, to the vessel wall into which shunt 100 is inserted. The shunt's elasticity permits at least a portion of tube body 108 to be stretched or lengthened along its length while reducing a dimension of shunt 100 which is transverse or substantially perpendicular to the shunt's longitudinal axis (such as the internal and external circumferences and diameters of shunt 100). More particularly, the tube material is selected so at least the outer circumference and diameter of end regions 102 and 140 can be reduced by about half, when the end region is lengthened or stretched in a direction away from central region 130 along axis A. Additionally, the material of tube 108 is sufficiently flexible and kink-resistant such that tube 108 may be flexed or bent about its width without kinking, and to allow atruamatic insertion of tube 108 into a vessel. Tube 108 is also fluid and gas impermeable to provide a leak-free conduit 126.

Accordingly, the tube material preferably comprises a monofilament material, such as braided polyester, impregnated with an elastomeric material, such as silicone, latex, or other similar materials. A suitable braided polyester material is available from Atkins & Pearce of Covington, Ky. The cross-hatched texture of the woven fabric of the preferred tubing material aids in securing the outer surface of the shunt 100 in the vicinity of the end regions 102 and 140 against the vessel walls. A suitable elastomeric material is available from Nusil Technology of Carpinteria, Calif. It should be understood, however, that any impermeable, elastic material that is biologically compatible and, when formed into a tube, reduces in cross-sectional circumference upon lengthening or stretching of the tube, is suitable for the shunts of the present invention.

Referring again to FIGS. 1A and 1B, shunt 100 further includes positioning stylus receptacles 110 and 150 disposed adjacent to end regions 102 and 140, respectively, of tube body 108 for receiving a stylus 120 (FIG. 1B), such as a wire or rod, to aid in manipulating shunt 100 into position within a vessel. Generally, positioning receptacles 110 and 150 are at least partially integrally formed with tube body 108 and have closed ends 112 and 152, respectively, and an open ends 116 and 156, respectively, and closed surfaces therebetween to define cavities 114 and 154 which may be in the form of a tube, slot, pocket or channel. Positioning receptacles of the present invention may vary in size, length, and position relative to the end and central portions of the shunt tube body 108. For example, receptacles 110 and 150 of FIGS. 1A and 1B are integrally mounted to and extend substantially linearly along upper wall portion 134 of tube 108 from the respective tips 104, 144 to approximately mid-way to respective tapered areas 106, 146. Various other embodiments of positioning receptacles are discussed below with respect to FIGS. 10–14.

Shown operatively received within receptacle 110 in FIG. 1B is a hand-held shunt positioning stylus 120. Stylus 120 may be a pre-formed, substantially rigid rod having a pre-selected bend or angle (see FIG. 3) or curve, as shown in FIG. 1B, and a suitable length, preferably about 10 to 20 cm, to accommodate a particular surgical access site or patient anatomy. Alternately, stylus 120 may consist of a semi-rigid but malleable wire that may be optimally shaped at the time of surgery and thereafter reshaped if needed during the surgery for repositioning the shunt in the same vessel or inserting the shunt in another vessel. Stylus 120 may also have a handle (not shown) to allow better gripping and control of the stylus.

The lengthening of tube 108 along its longitudinal axis A and the contraction or reduction of the circumferential dimensions of end regions 102 and 140 when stylus 120 is employed are schematically illustrated in FIG. 1B. The reduced circumferences and diameters which result when end regions 102 and 140 are lengthened permit oblique tips 104 and 144 of end regions 102 and 140, respectively, to be inserted through a small incision in a vessel and to be delivered and extended within the lumen of the vessel on either side of the incision. When end regions 102 and 140 are permitted to axially contract to their pre-formed length, as shown in FIG. 1A, end regions 102 and 140 will expand towards their biased, natural circumferential dimensions and press against the interior walls of the shunted vessel to form a fluid-tight seal.

Prior to beginning the surgical procedure to install the shunt, a shunt device of appropriate size is selected for the vessel to be shunted. The size of the shunt, and particularly the circumferences of a shunt when in respective relaxed and stretched conditions, are selected based on the inner diameter of the vessel or tissue structure into which the shunt is to be inserted. More specifically, the central region of the shunt, when in a relaxed condition, should have an outer circumference that approximates the circumference of the inner wall of the vessel so that the shunt will fit within the lumen of the target vessel. Furthermore, in such a relaxed condition, the central region of the shunt should have an internal area which will allow blood flow there through to approximate the natural fluid flow volume through the vessel. Additionally, the circumferences of the end regions, when in a relaxed or biased condition, must be large enough so that the end regions, once inserted into the vessel and released, expand to apply sufficient pressure against the vessel wall to form a fluid-tight seal between the outer surface of the shunt and the inside vessel wall.

Although suitable for a variety of vascular procedures, the shunt of the present invention is most suitable for a carotid endarterectomy procedure and an anastomosis in a coronary artery bypass graft procedure. Accordingly, shunts of the present invention would be typically sized for such procedures. The following dimensions for shunts, for insertion into coratid and coronary arteries, are intended to be exemplary, with variations. For example, the average internal diameter of human carotid arteries is about 4 mm for external carotid arteries, 6 mm for internal carotid arteries, and 12 mm for common carotid arteries. The average incision length in a carotid artery for performing an endarterectomy procedure is from about 3 to 4 cm, preferably from about 3.4 to about 3.8 cm, and more preferably about 3.6 cm. Thus, a shunt of the present invention for employment in a carotid endarectomy procedure has the following approximate dimensions: an end-to-end length of about 7 to 9 cm; a central portion length of about 2 to 4 cm, an outer diameter of about 4 to 8 mm, and an internal diameter of about 3 to 7 mm for center portion 130; an axial length of 1 cm for each tapered region 106, 146; an axial length of from 1 to 2 cm, an outer diameter of about 4 to 12 mm, and an internal diameter of about 1 to 4 mm for each end region 102, 140; an internal diameter of from about 0.25 to 0.75 mm for receptacle pockets 114 and 154; and an angle of 30 to 60 degrees from the axis defined by the length of the shunt for the oblique cut of each tip 104, 144.

The average internal diameter of human coronary arteries is from about 1 to 3.5 mm, and the length of an arteriotomy for an anastomosis in a coronary artery, for example, is from about 3 to 5 mm. Thus, for surgical procedures involving coronary arteries, a shunt of the present invention has the following approximate dimensions: an end-to-end axial length of about 1.5 to 3 cm; an axial length of about 1 to 2.5 cm, an outer diameter of about 1 to 3.5 mm, and an internal diameter of about 0.75 to 3 mm for central region 130; an axial length of 0.1 to 0.25 cm for each tapered region 106 and 146; an axial length of from 0.25 to 0.5 cm, an outer diameter of about 2 to 5 mm, and an internal diameter of about 1.5 to 4.5 mm for the end regions 102 and 140; an internal diameter of about 0.20 to 0.75 mm for receptacle pockets 114 and 154; and an angle of 30 to 60 degrees for the oblique cut of tips 104 and 144.

Referring now to FIGS. 2–9 an exemplary method of use of a shunt of the present invention is illustrated and described. Specifically, the implantation and removal of the inventive shunt in a blood vessel is described primarily in the context of an endarterectomy procedure. However, the procedure described herein is intended to be exemplary and in no way limits the devices and methods of the present invention.

After a determination is made as to the appropriate incision site on the target vessel 230, the vessel 230, as shown in FIG. 2, is then preferably occluded to temporarily arrest the flow of blood while an incision 234, called an arteriotomy, is made in the target vessel using conventional instruments such as scalpel 225. There are various means known in the art for temporarily occluding a vessel. One such means are small vascular clamps, which are commonly used in endarterectomy procedures. As shown in FIG. 2, a vascular clamp 233 is placed on each side of incision 234; however, one clamp on the proximal side or upstream side of the incision may be sufficient. Another occlusion technique (not shown), which is often used during an anastomosis for coronary artery bypass graft and may be used with the present invention, involves tying a suture around the outside of the target vessel. An incision 234 is then made in vessel 230 to expose the vessel lumen 232 on one end of incision 234 and the vessel lumen 236 at the opposing end of incision 234.

Figure 3:
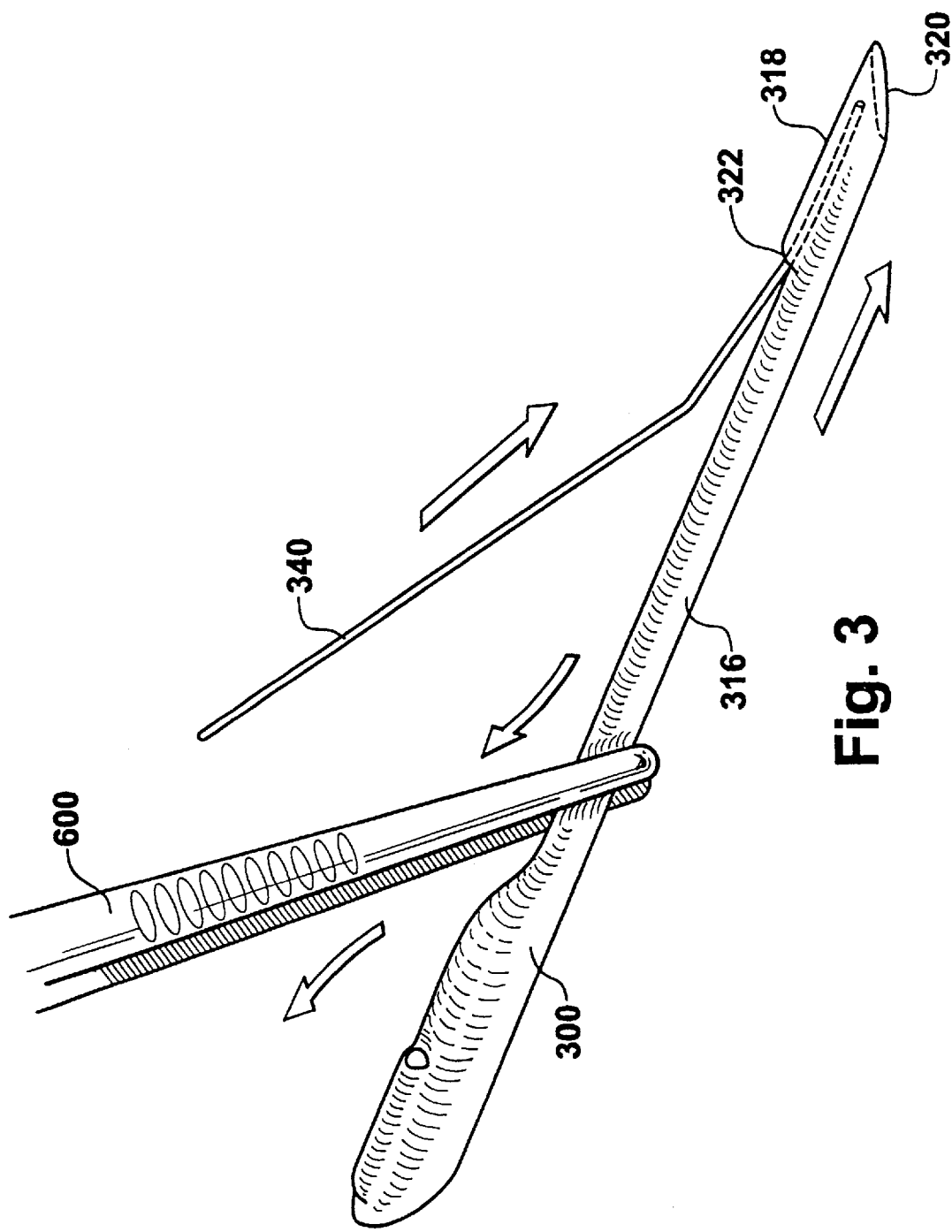
FIG. 3 is a diagram of the embodiment of the shunt apparatus of FIGS. 1A and 1B being held by a pair of surgical forceps while being stretched by a stylus of the present invention.

Next, a shunt 300, such as that illustrated in FIG. 3, is provided which may have its inner and outer surfaces heparinated prior to implantation in the vessel 232 to reduce clotting due to interaction between the patient's blood and the material of shunt 300. While grasping the central portion 316 of shunt 300 with a pair of forceps 600, a shunt positioning tool 342, or between a thumb and forefinger, a stylus, such as positioning wire 340 shown in FIG. 3, is inserted into a first receptacle 322 in an end portion 318 of shunt 300. Pushing on wire 340 while pulling or fixing the position of central portion 316, as indicated by the respective arrows, causes end portion 318 to stretch or lengthen. This elongation in turn reduces the cross-sectional dimensions of end portion 318. Specifically, the circumference and diameter of the outer surface of end portion 318 is caused to collapse or become reduced to permit insertion of oblique tip 320 into lumen 232, as shown in FIG. 4A. The lengthening of end portion 318 should be continued until substantially the entirety of end portion 318 is positioned within blood vessel 232. Stylus wire 340 may then be withdrawn to permit end region 318 to axially contract along the longitudinal axis of shunt 300 and to circumferentially expand to its natural, biased dimension, lodging itself against the vessel wall of vessel lumen 232.

FIG. 4B shows an alternate means of inserting shunt 300 into a coronary artery in a procedure for bypassing an occluded coronary artery with a fresh supply of blood from the left internal mammary artery using a shunt positioning tool 342. The shunt positioning tool 342 provides a superior means of grasping and manipulating the shunt 300 within the vessel 232 during the anastomotic procedure than does a simple pair of forceps 600. In particular, the shunt positioning tool 342 prevents inadvertent rotation or slippage of the shunt 300 during manipulation of the shunt 300.

Figure 4C:
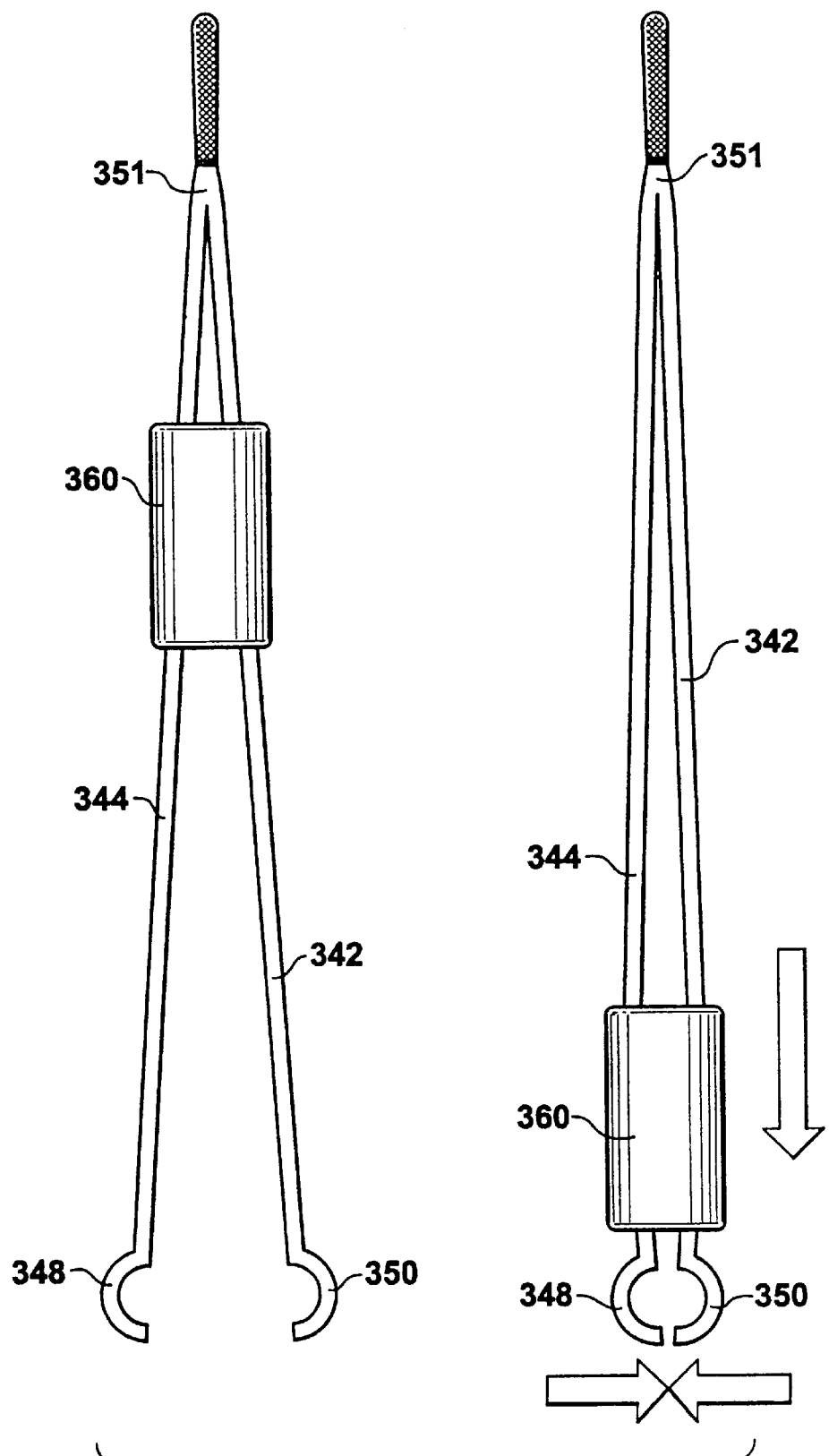
FIG. 4C is a shunt positioning tool of the present invention having first and second elongate arm members fixed relative to each other at a distal end of the arm members.

The construction of a shunt positioning tool 342 of the present invention is shown in detail in FIG. 4C. The tool 342 is shown in its "opened" and "closed" positions. The tool 342 comprises a first elongate arm 344 and a second elongate arm 346 wherein the first and second arms 344, 346 are pivotably fixed at a proximal end of the shunt positioning tool 342 relative to each other. The first and second arms 344, 346 include a first and second distal ends 348, 350 to which are configured to conformingly engage the cylindrical body of the shunt 300 of the present invention when the first and second arms 344, 346 are biased to a closed position relative to each other. For the embodiment shown in FIG. 4C, the shunt positioning tool 342 is configured similarly to an elongate pair of tweezer forceps with a special shunt engaging distal end. It can be seen that the pivotable attachment point 351 may be located at an intermediate point on the elongate arm members so that device operates in a scissors-like fashion. A number of other configurations for the shunt positioning tool are also possible without departing from the spirit of the invention.

The distal ends 348, 350 of the first and second elongate arms 344, 346 are configured having a semi-cylindrical configuration which is sized to engage the outer surface of the shunt conformingly. The device may also include a locking ring 360 which may be slid distally along the first and second arms 344, 346 to hold the arms in a closed position when grasping the shunt 300.

As seen in FIG. 4B, the axial length of the semi-cylindrical distal ends 348, 350 of the shunt positioning tool 342 should be no greater than the length of the center portion 316 of the shunt 300. Preferably, the axial length should be kept relatively short to prevent interference with the walls of the incision 365. Keeping the length short will also allow maximum maneuverability of the shunt 300 and the tool 342 within the vessel 332 during the procedure.

Figure 4D:
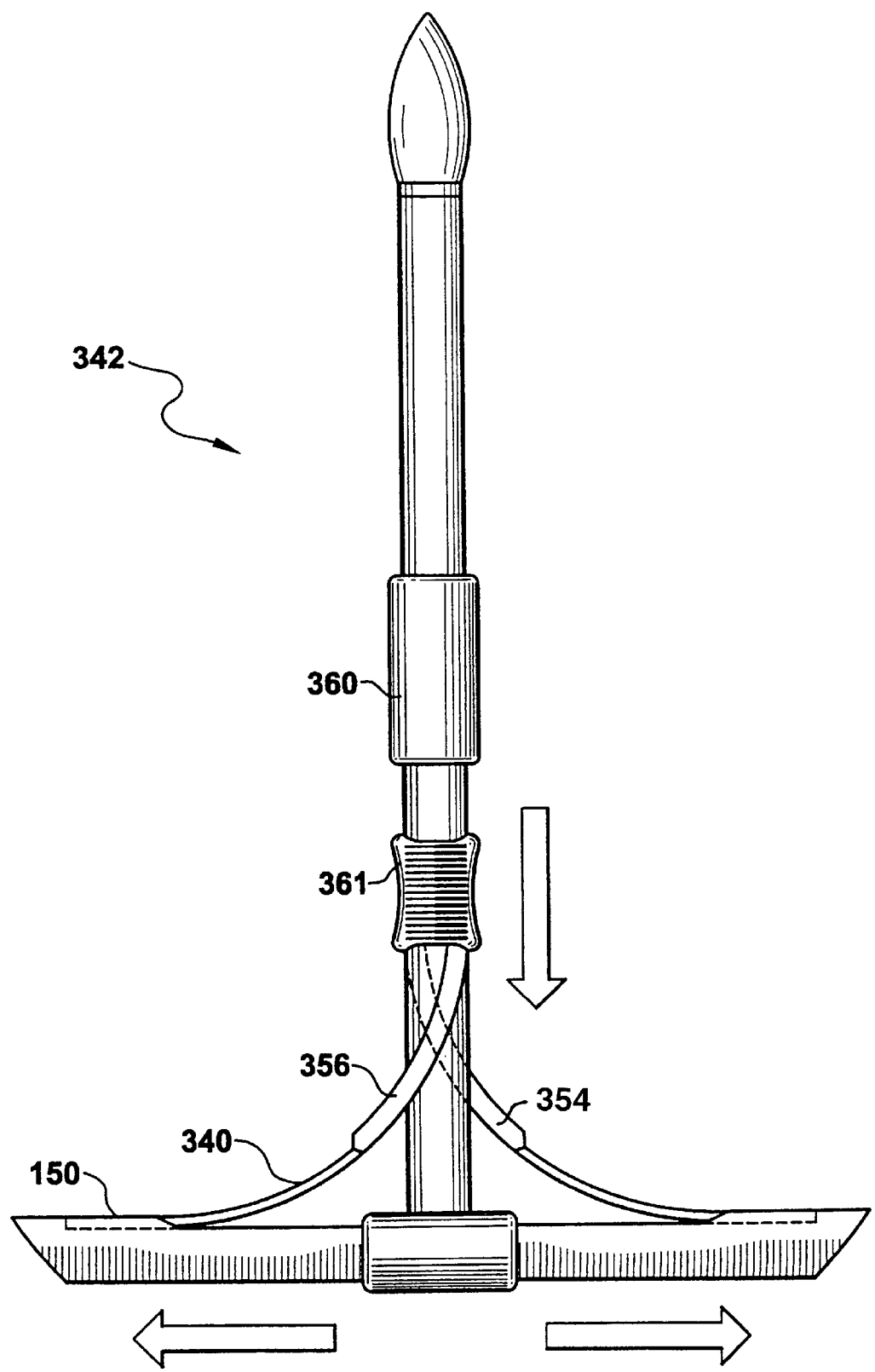
FIG. 4D is the shunt positioning tool of FIG. 4C including a pair of curved wire guides fixed to the first and second elongate arm members.

FIG. 4D shows another shunt positioning tool 342 of the present invention wherein the shunt 300 is securely held in the distal ends 348, 350 of the tool 342. The shunt position tool 342 further includes first and second wire guides 354, 356 which are fixed to the first and second arms 344, 346 proximal to the distal ends 348, 350 of the respective arms. The wire guides 354, 356 serve as a means to properly guide a wire or stylus 340 into receptacles 110 or 150. Preferably, the wire guides are configured from a curved piece of tubing which evenly translates distal movement of the wire 340 into lateral movement of the wire 340. When the wire 340 is in engagement with the receptacle 110, for example, lateral movement of the wire will cause axial stretching and contraction of the first end 362 of the deformable shunt 300. The tool 342 may also further include a thumb tab 361 fixed to the proximal end of one or both wires 340 which allows easy, one-handed longitudinal elongation and contraction of the shunt 300 for emplacement of the device within a vessel.

Figure 4F:
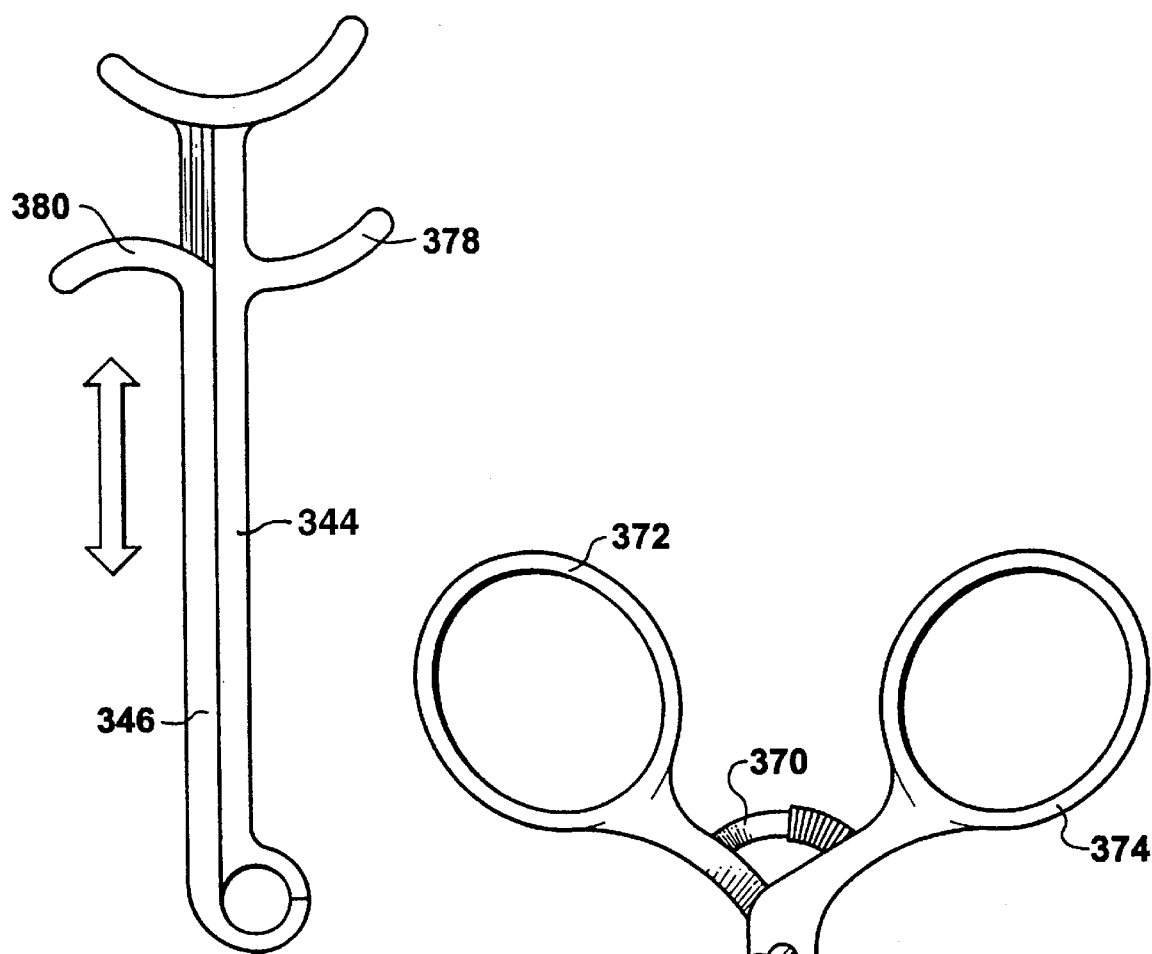
FIG. 4F is a shunt positioning tool of the present invention wherein first and second elongate arm members are slidingly connected relative to each other.

FIG. 4F is an alternate embodiment of the shunt positioning tool 342 wherein it is configured with pivotable attachment point 351 intermediate the distal and proximal ends of the first and second 344, 346 elongate arm members. A latching tooth portion 370 is included to securely hold the distal ends 348, 350 in a closed position if desired.

Figure 4E:
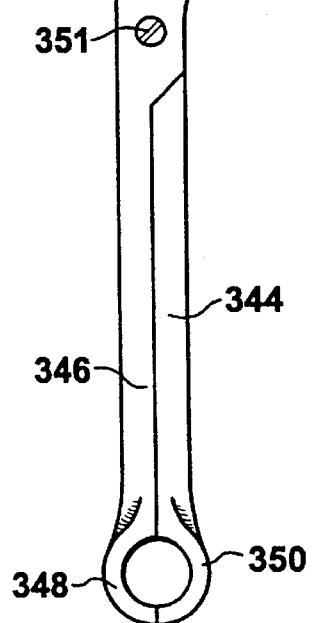
FIG. 4E is a shunt positioning tool of the present invention wherein the first and second elongate arm member are hingedly connected at an intermediate point on the arm members.

FIG. 4E is an alternate configuration of a shunt positioning tool 342 of the present invention wherein first and second elongate arm members 344, 346 are slidable relative to each other from an "open" to a "closed" position. The first and second arms 344, 346 may also be provided with handles of thumb knobs 378, 380 to aid in the manipulation of the device around a shunt. The device may also be provided with a locking device to lock the tool 342 in place around a shunt.

Figure 5:
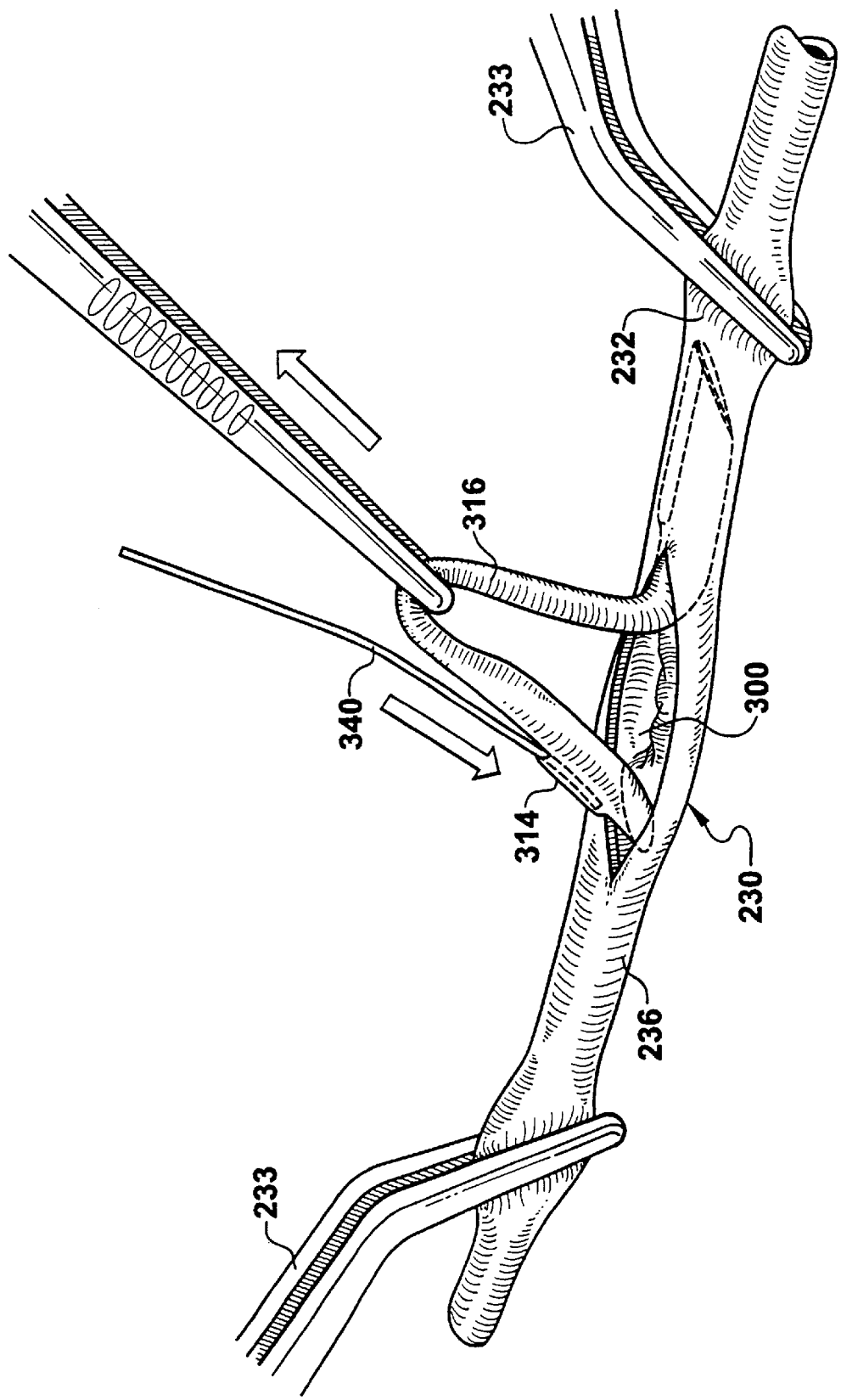
FIG. 5 is a diagram showing the other end of the shunt apparatus of FIGS. 1A and 1B being inserted into the vessel lumen on the other side of the incision in the vessel.
Figure 6:
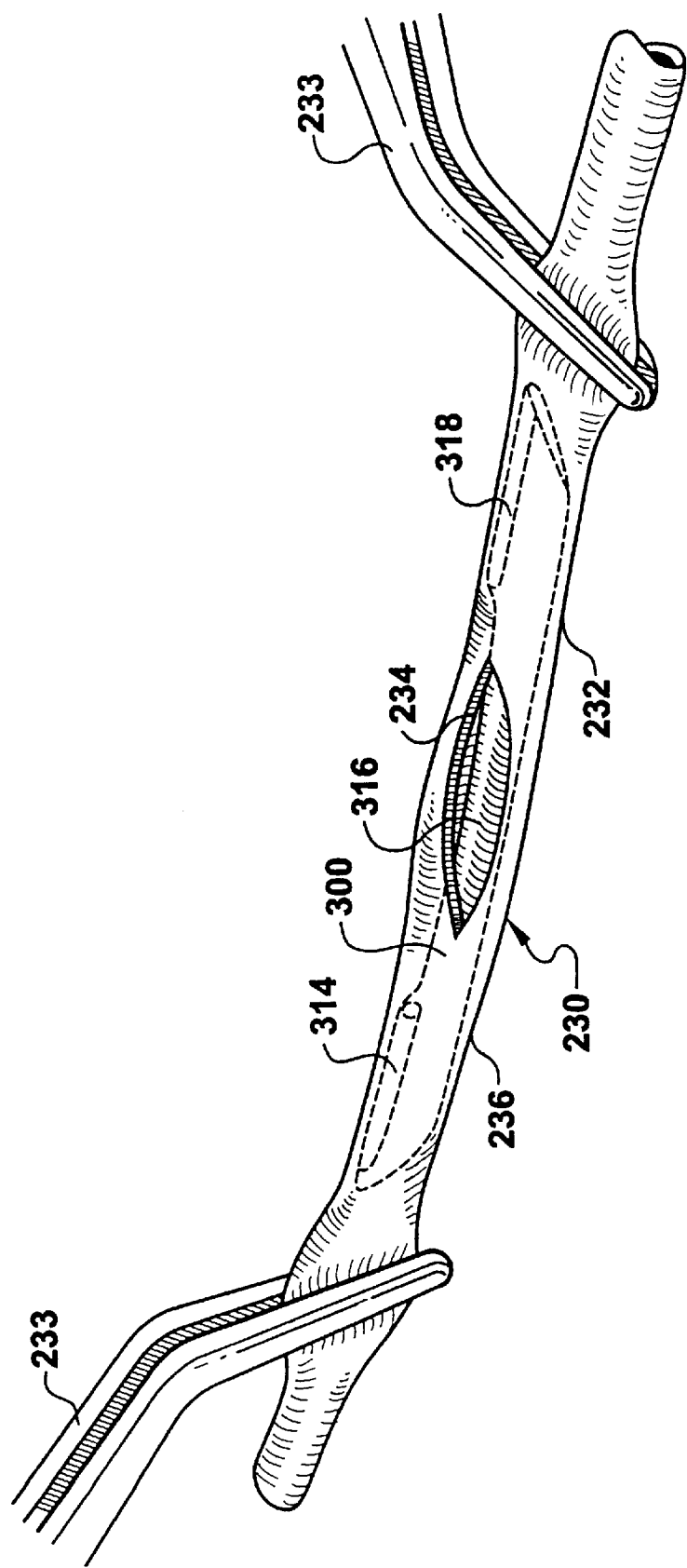
FIG. 6 is a diagram showing the shunt apparatus of FIGS. 1A and 1B in its functional position within the incised vessel.

Returning to a description of a method of inserting a shunt of the present invention, FIG. 5 illustrates that, following insertion of the first end 318 of shunt 300 into the vessel lumen 236 using either a traditional grasping method or the shunt positioning tool 342 of the present invention, a wire 340 is then inserted into receptacle 314 and the central portion 316 is grasped to similarly stretch and insert end portion 314 into lumen 236. After shunt 300 has been acceptably positioned, wire 340 is then removed from receptacle 314 and vascular clamps 233 are removed from vessel 232 to allow blood to flow in its natural direction through shunt 300. In FIG. 6, end portions 314 and 318 are shown fully deployed within lumens 236 and 232, respectively, and central portion 316 is nestled into blood vessel 230 in the vicinity of incision 234.

The determination as to whether shunt 300 is first inserted into the portion of vessel which is downstream (i.e., the portion distal to incision 234) or upstream (i.e., the portion of vessel proximal to incision 234) of the natural direction of flow of the bodily fluid may depend on several factors, including the procedure being performed (e.g., endarterectomy, coronary artery bypass grafting, etc.), the vessel being shunted, the patient's anatomy, and surgeon preference, and will likely vary from vessel to vessel and from case to case.

Figure 7:
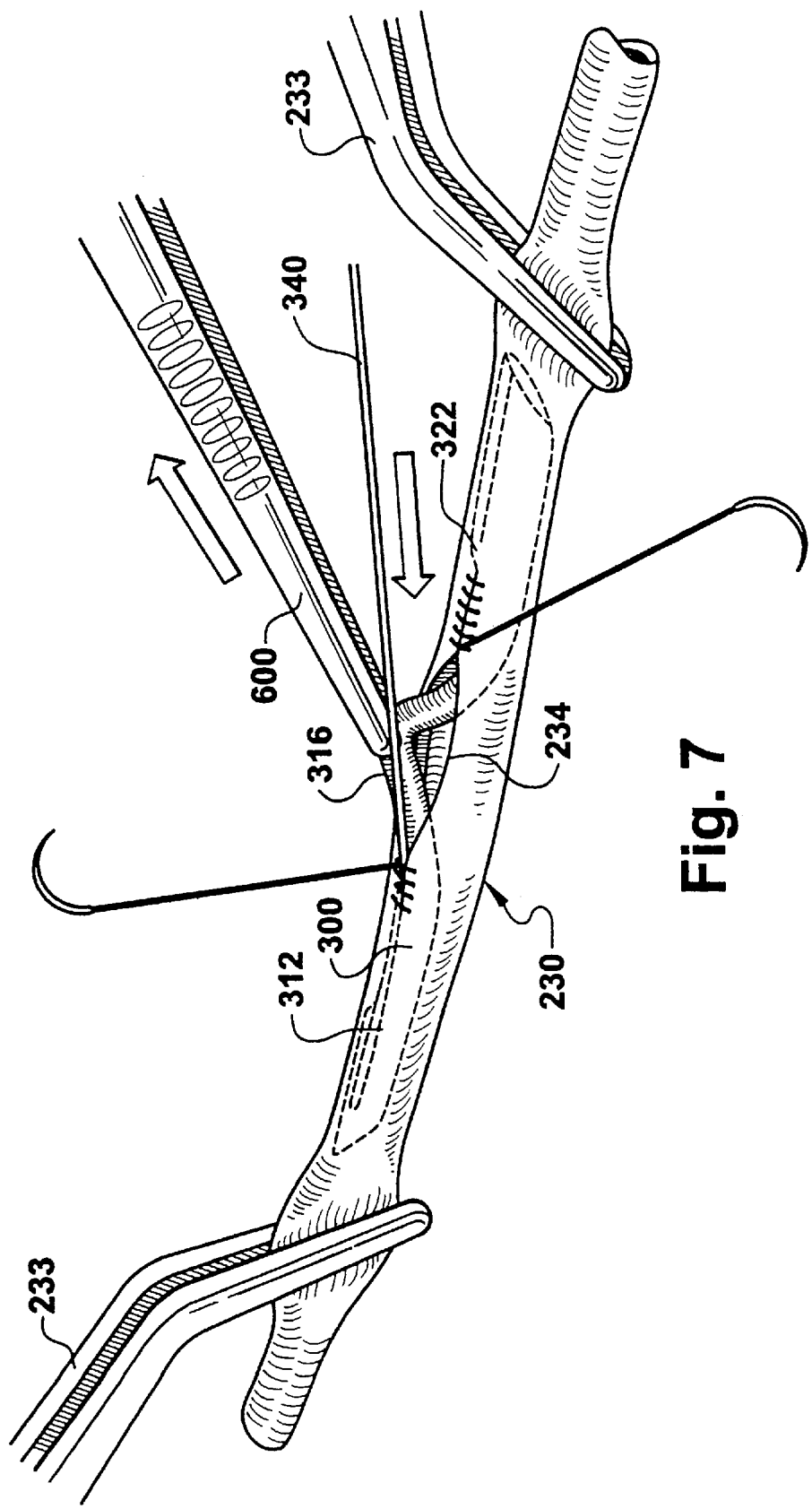
FIG. 7 shows the shunt apparatus of FIGS. 1A and 1B being repositioned within the vessel during suturing of the incision.

Should the need arise, shunt 300 may be repositioned during the surgical procedure by reinserting wire 340 into either receptacle 312 or 322 to lengthen and reposition end portions 314 or 318, respectively, within the vessel 230, as illustrated in FIG. 7. Forceps 600 may be required to grasp central portion 316 and hold shunt 300 steady while wire 340 is reinserted and used to stretch the appropriate end portion. Repositioning of the shunt may be performed prior to suturing or as incision 234 is sutured and the incised opening is reduced in size. The shunt positioning device 342 illustrated in FIGS. 4(B–D) may also be used to rapidly manipulate the shunt as shown in FIG. 4B.

Figure 8:
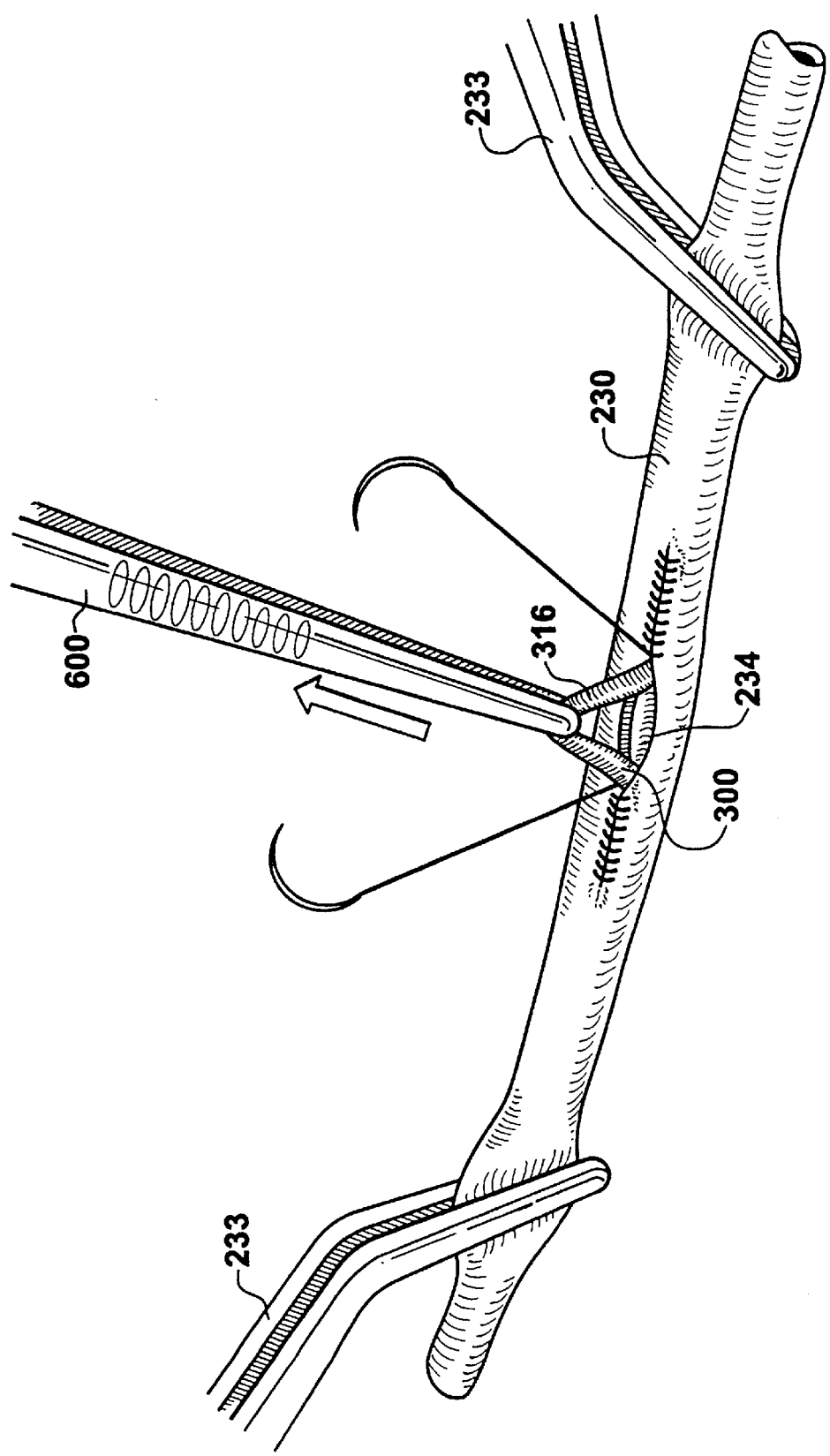
FIG. 8 shows the shunt apparatus of FIGS. 1A and 1B being removed from the vessel through a partially sutured incision.
Figure 9:
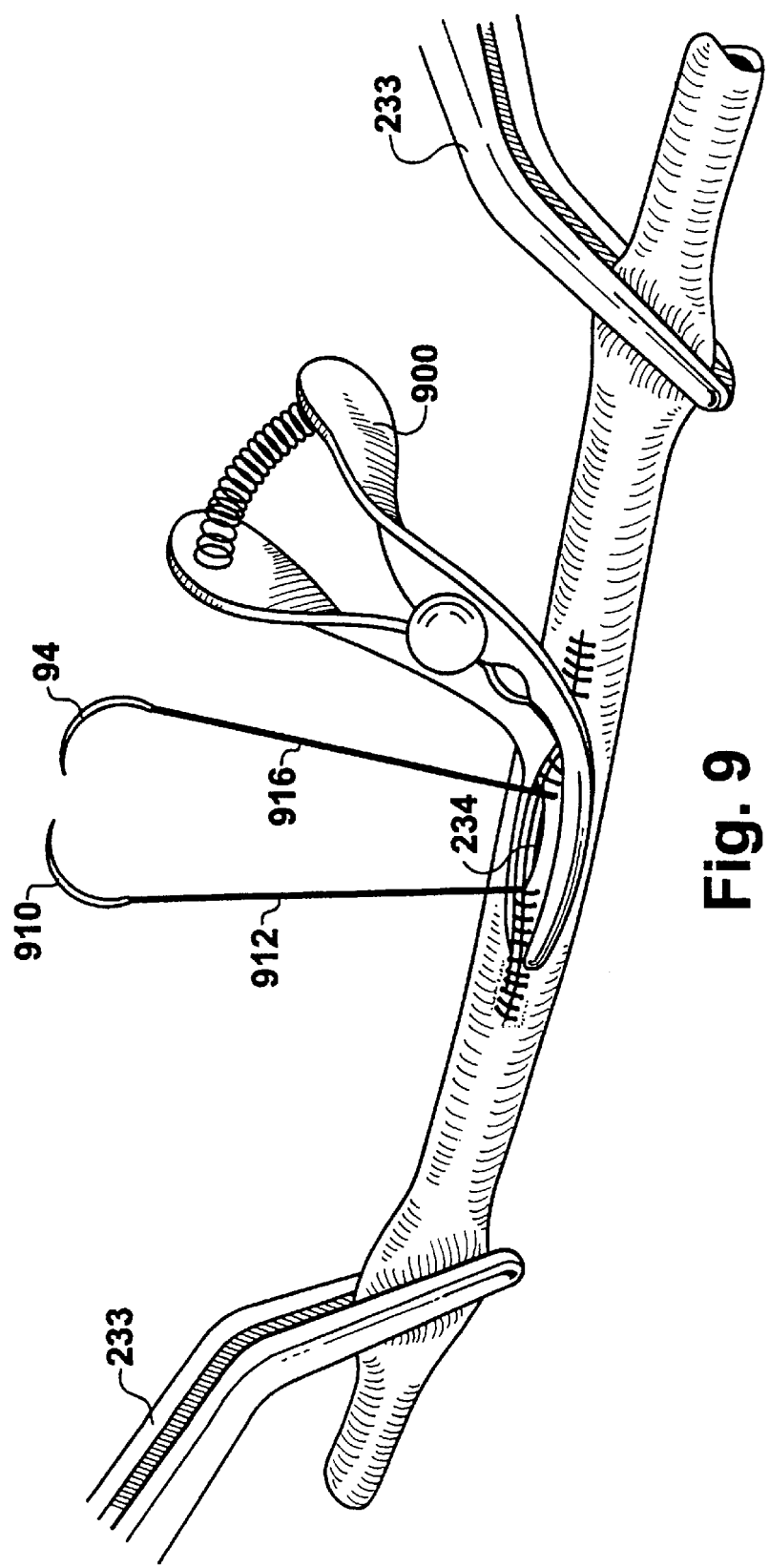
FIG. 9 shows the incision in the vessel being clamped and sutured for final closure after removal of the shunt apparatus of FIGS. 1A and 1B.

To remove shunt 300, FIG. 8 demonstrates that the incision 234 is sutured leaving a small opening to permit removal of the shunt. Forceps 600 or other previously discussed positioning tools are then used to grasp shunt 300 by central portion 316 and pull the shunt out through the opening remaining in vessel 230. In FIG. 9, a side-biting clamp 900 is used to hold closed the remaining opening in incision 234 as suturing needles 910 and 94 are used to suture the remainder of incision 234 shut with sutures 912 and 916.

Examples of other surgical procedures in which the shunt would be implanted in a manner similar to that described above, with minor modifications which can be readily understood and appreciated by those skilled in the art, include, but are not limited to, coronary artery bypass grafting and thoraco-abdominal aortic reconstruction.

Figure 10:
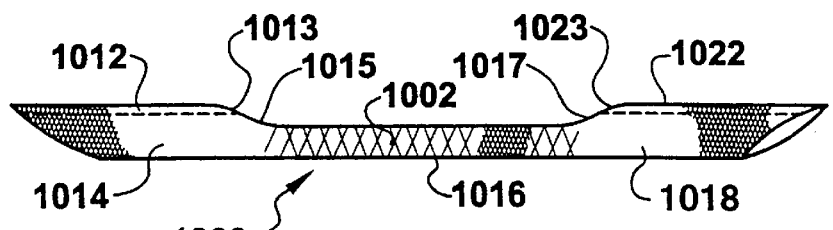
FIG. 10 is a diagram of another embodiment of the shunt apparatus of the present invention wherein the positioning receptacles are located on the inside surface of the ends of the main shunt tube and the central portion of the shunt includes a reinforcing member.

Turning now to FIGS. 10–15, there are illustrated views of alternate embodiments of the present invention. For example, FIG. 10 illustrates a shunt 1000 having a central portion 1016, and end regions 1014 and 1018 similar to that of shunt 100 of FIGS. 1A and 1B. The positioning receptacles 1012 and 1022 (illustrated in phantom) of FIG. 10 differ from those of FIGS. 1A and 1B in that they are disposed on the inner, rather than outer, surface of end regions 1014 and 1018 of shunt 1000. Additionally, the length of receptacles 1012 and 1022 are coincident with the length of end regions 1014 and 1018, and their respective openings 1013 and 1023 are coincident with the outer surface of the shunt at respective tapered areas 1015 and 1017. The embodiment of FIG. 10 also employs a reinforcing member, such as a metal ribbon or coil 1002, disposed along a central region 1016 to prevent the central region from becoming crimped during insertion or repositioning of shunt 1000, thereby causing the flow of fluid through shunt 1000 to be pinched off.

Figure 11:
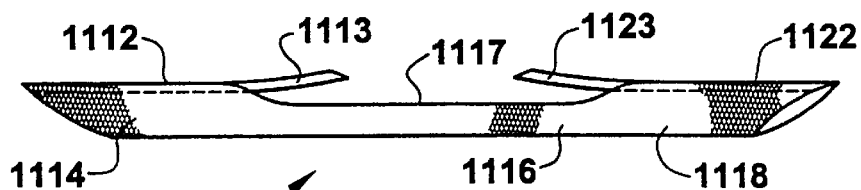
FIG. 11 is a diagram of embodiment of the present invention wherein elongated positioning receptacles extend from the inside surface of the ends of the main shunt tube.

FIG. 11 illustrates another shunt 1100 of the present invention wherein receptacles 1112 and 1122 are disposed along the inner surface of end regions 1114 and 1118, as in FIG. 10, but are longer than the end regions and extend, in the form of tube portions 1113 and 1123, respectively, past the outer surface of shunt 1100, inwardly or proximally with respect to the shunt tube, and over a portion of central region 1116. Preferably, when shunt 1100 is operatively positioned within a vessel, tube portions 1113 and 1123 extend past the respective apexes of the incision and are readily visible and accessible for insertion of a stylus into receptacles 1112 and 1122.

Figure 12:
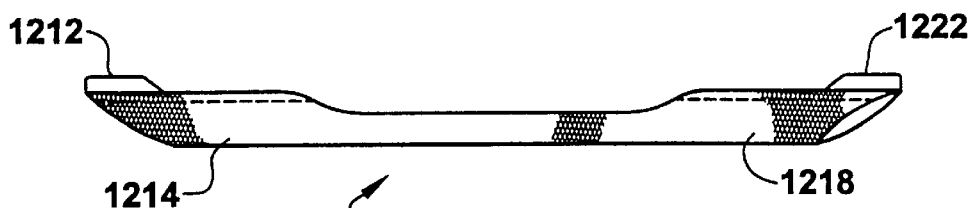
FIG. 12 is a diagram of yet another embodiment of the present invention wherein short positioning receptacles are located on the outside surface of the ends of the main shunt tube.
Figure 13:
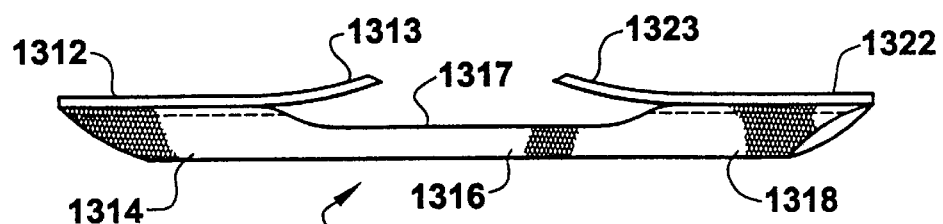
FIG. 13 is a diagram of another embodiment of the present invention wherein elongated positioning receptacles extend along the outside surface of the ends of the main shunt tube.
Figure 14:
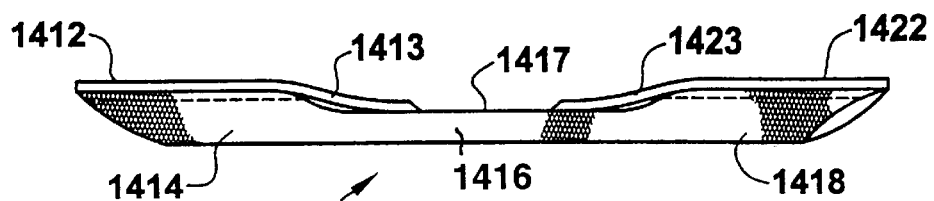
FIG. 14 is a diagram of another embodiment of the present invention wherein elongated positioning receptacles extend along the outside surface of the ends of the main shunt tube and attach to the outside surface of the central portion of the main shunt tube.

FIGS. 12–14 illustrate further embodiments of the present invention wherein the respective stylus receptacles are disposed along the outer surfaces of at least a portion of the end regions, similar to the embodiment of FIGS. 1A and 1B, and all having closed ends coincident with the tip ends. In FIG. 12 the receptacles 1212 and 1222 are disposed along only about one fourth to less than about one half the length of end regions 1214 and 1218 but may extend over more or less thereof.

In the embodiment of FIG. 13, receptacles 1312 and 1322 are disposed along the entire length of end regions 1314 and 1318, respectively, and, similar to the embodiment of FIG. 11, further comprise tubular extensions 1313 and 1323, respectively, which extend proximally over at least a portion of recessed area 1317 of central region 1316. Here, tubular extensions 1313 and 1323 are each shown to extend over about one third of recessed section 1317 but may extend over more or less thereof.

FIG. 14 illustrates an embodiment wherein receptacles 1412 and 1422 are disposed on the outer surface of shunt 1400 along the length of end regions 1414 and 1418 and terminate in proximally extending tubular extensions 1413 and 1423, respectively. Unlike the embodiment of FIG. 13, the ends of tubular extensions 1413 and 1423 are fixed to a portion of the recessed area 1417 of central region 1416. Enough space remains between the fixed ends 1413 and 1423 so that a stylus may be received in either receptacle 1412 or 1422.

Preferably, the positioning receptacles of the present invention are collapsible so that, if disposed on the outer surface of the shunt, they do not interfere with the fluid tight sealing between the shunt and the vessel wall. On the other hand, if disposed along the inner surface of the shunt, collapsible positioning receptacles will not impede the flow of fluid through the shunt lumen. To this end, the positioning receptacles of the present invention may be made of material similar to that suggested for the shunt body.

Figure 15A:
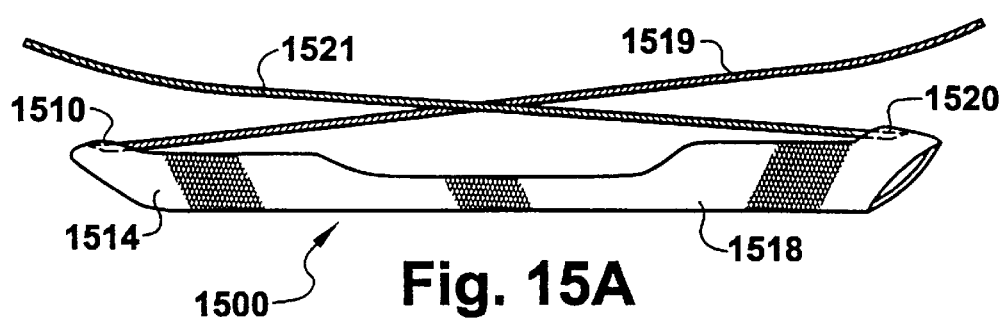
FIG. 15A is a diagram of another embodiment of the present invention having a stylus integrally coupled to each end of the shunt.
Figure 15B:
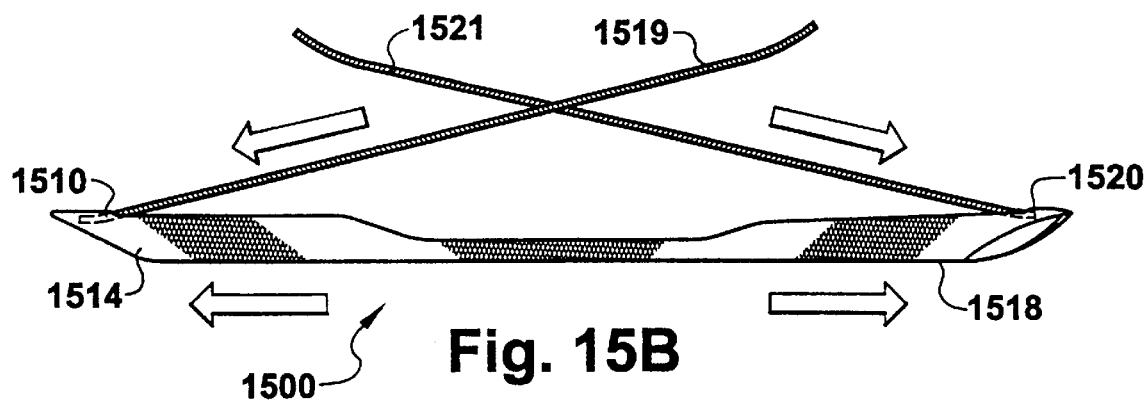
FIG. 15B is a diagram of the shunt of FIG. 15A, wherein elongation of the shunt is accomplished by stretching apart the ends of the shunt by means of the stylets.
Figure 15C:
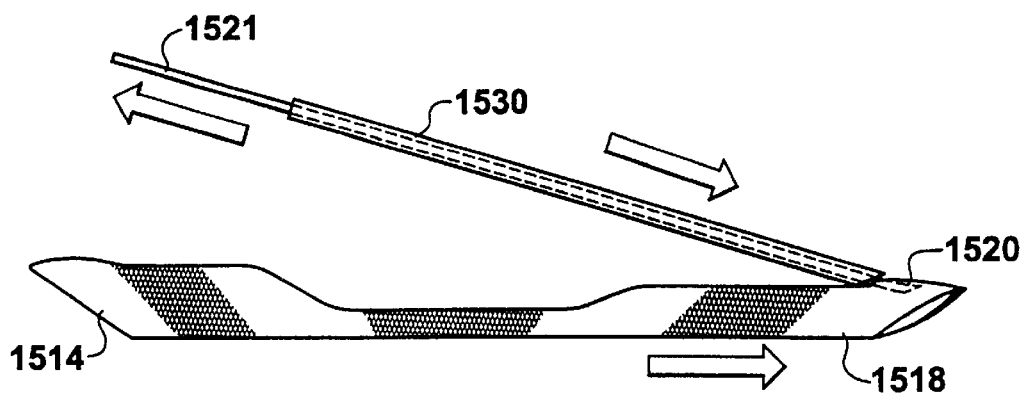
FIG. 15C is a diagram of the shunt of FIG. 15A, wherein elongation of the shunt is accomplished by means of passing a slender sleeve over the stylus.

The embodiment of FIGS. 15A and 15B differ from the others previously described in that shunt 1500 does not have any positioning receptacles, but rather, has stylets 1519 and 1521 integrally coupled at one end thereof to shunt tips 1510 and 1520, respectively. Stylets 1519 and 1521 may be pre-formed or malleable, and have a selected length suitable for the surgical procedure being performed. Stylets 1519 and 1521 may consist of a wire that is looped through or otherwise fastened to the most distal portion of tips 1510 and 1520. As illustrated in FIG. 15B, the two stylets may be used in tandem by simultaneously exerting a distally directed force, as indicated by the arrows, on each of them to stretched the respective end regions 1514 and 1518. Alternatively, as shown in FIG. 15C, a thin positioning tube 1530 may be passed over one of the wire stylets 1519 (not shown), 1521 while gently pulling on the stylet to stretch the respective end region 1514, 1518.

In an alternate configuration, the wire stylet may comprise a relatively stiff material which is configured having a sharpened distal end (not shown). In use, the distal end is used to penetrate the body wall of the shunt at one or both ends of the shunt at a relatively oblique angle. The shunt is preferably configured from a relatively soft silicone or elastomer which will allow penetration by the wire stylet yet still remain impermeable to fluid flow should the stylet accidentally completely penetrate the body wall of the shunt. The use of a sharpened stylet eliminates the need for a receptacle disposed on the first and/or second ends of the shunt while still providing a means for longitudinal elongation and contraction of the shunt.

The overall shape of the shunt embodiments illustrated in FIGS. 1–15 is that of an irregular cylinder. However, the present invention is not limited to a cylindrical device but can vary significantly within the confines of a generally tubular structure. For instance, the end portions of the shunt may be frustoconical in shape or flared to form a hyperboloid in one sheet with the central portion. Irrespective of shape, the various shunts of the present invention should be elastically deformable so as to be expandable along their lengths and substantially contractible along their widths to facilitate insertion, positioning and removal of the shunt in a vessel, to minimize trauma to the vessel, and to easily conform to the contours of the vessel into which the shunt is implanted.

The above-described components of the present invention or a combination thereof may be provided in a surgical kit. Such a kit may include, for example, one or more shunts of varying sizes, with positioning receptacles having various configurations and one or more positioning stylets. It may also include a shunt positioning tool as herein described. In another embodiment, such a kit may include one or more shunts having integrally attached stylets and positioning tubes.

Although only certain embodiments have been described in detail, those having ordinary skill in the art will certainly understand that many modifications are possible without departing from the teachings thereof. All such modifications are intended to be encompassed within the following claims.

What is claimed is:

1. A shunt device for implantation in a fluid-carrying vessel or tubular tissue structure, comprising:
  an elastically deformable, generally tubular body, said tubular body having upper and lower opposing wall portions, a central portion and first and second end portions, said first and second end portions having a relatively larger circumference than said central portion, wherein said lower wall portion extends substantially linearly along said tubular body and said upper wall portion includes first and second tapered wall sections that together define a recessed section of said upper wall portion, said first tapered wall section extends between said first end portion and said central portion and said second tapered wall section extends between said second end portion and said central portion, and said central portion and said first and second end portions collectively define a longitudinal axis whereby stretching at least one end portion along said longitudinal axis, during implantation or delivery of said tubular body, results in a reduction in a dimension of said tubular body which is transverse to said longitudinal axis; and means for facilitating the insertion and position of said shunt device within a vessel or tubular structure.

2. The shunt device of claim 1 wherein a transverse dimension of each of said first and second end portions is greater than a transverse dimension of said central member.

3. The shunt device of claim 2 wherein said transverse dimension of said end portion is reduced by about half when said end portion is stretched.

4. The shunt device of claim 3 wherein said transverse dimension of said central member is an outer diameter, said outer diameter of said central member being substantially the same as the inner diameter of the vessel into which said shunt device is to be implanted.

5. The shunt device of claim 1, wherein said tubular body is constructed of a braided fabric impregnated with an elastomer.

6. The shunt device of claim 5, wherein said braided fabric is monofilament polyester and said elastomer is silicone.

7. The shunt device of claim 1, further comprising a reinforcing member having an axis and disposed along said central portion such that said axis of said reinforcing member is substantially coincident with said longitudinal axis of said tubular body.

8. The shunt device of claim 7 wherein said reinforcing member is a coil.

9. The shunt device of claim 4 wherein the vessel into which said shunt device is to be implanted is a carotid artery, and wherein the first and second end portions have an outer diameter of about 4 to 12 mm and the center portion has an outer diameter of about 2 to 6 mm.

10. The shunt device of claim 9, wherein the shunt has an end-to-end axial length of about 7 to 9 cm.

11. The shunt device of claim 4 wherein the vessel into which said shunt device is to be implanted is a coronary artery, and wherein the first and second end portions have an outer diameter of about 1 to 3.5 mm, and the central portion has an outer diameter of about 2 to 5 mm.

12. The shunt device of claim 11 having an end-to-end axial length of about 1.5 to 3 cm.

13. The shunt device of claim 1 wherein said means associated with said tubular body for inserting and positioning said shunt device comprises first and second receptacles for receiving a stylus, wherein said first receptacle is adjacent said first end portion and said second receptacle is adjacent said second end portion.

14. The shunt device of claim 13 wherein said tubular body further comprises inner and outer body surfaces defining a body wall and wherein each of said first and second receptacles comprises a closed end, an open receptacle end, and a closed receptacle surface defining a stylus cavity.

15. The shunt device of claim 14 wherein each of said first and second end portions has a length and each of said first and second receptacles has a length and wherein each of said receptacles extends along at least a portion of said length of said end portion to which it is adjacent.

16. The shunt device of claim 15, wherein said receptacle length is less than said end portion length.

17. The shunt device of claim 15, wherein said receptacle length is substantially the same as said end portion length.

18. The shunt device of claim 15, wherein said receptacle length is greater than said end portion length and wherein said open end of each said receptacle extends proximally beyond said end portion to which it is adjacent.

19. The shunt device of claim 18, wherein each of said open ends is attached to said central portion.

20. The shunt device of claim 14 wherein said respective stylus cavities are disposed outside said body wall.

21. The shunt device of claim 14 wherein said respective stylus cavities are disposed within said inner and outer body surfaces.

22. The shunt device of claim 1 wherein said means associated with said tubular body for inserting and positioning said shunt device comprises a first stylus attached to said first end portion and a second stylus attached to said second end portion.

23. The shunt device of claim 22 further comprising at least one positioning sleeve configured to be passed over said first stylus and said second stylus.

24. The shunt device of claim 1 wherein said tubular body further comprises inner and outer body surfaces defining a body wall and said means associated with said tubular body for inserting and positioning said shunt device comprises a first stylus having a sharpened distal end adapted to penetrate said body wall.

25. The shunt device of claim 24 wherein said body wall comprises a relatively soft elastomeric material adapted for penetration by said first stylus.

26. A surgical shunt for shunting bodily fluids in a vessel, comprising:

an elastically deformable tube including distal and proximal ends, a center portion and closed upper and lower surfaces, wherein said closed upper surface includes first and second tapered wall sections that together define a recessed section of said upper surface, said first tapered wall section extends between said distal end and said central portion and said second tapered wall section extends between said proximal end and said central portion, defining a continuous, axially-disposed conduit extending completely through said distal and proximal ends and said center portion, and said lower surface extends substantially linearly along said tubular body, each of said distal and proximal ends having a circumference defined by a cross-section perpendicular to a longitudinal axis of said tube, and wherein a stretching of one end in an axial direction away from said center portion causes a corresponding reduction in said circumference of said one end to permit insertion of said one end into a vessel lumen, and wherein each of said ends is biased to a predetermined circumference such that said end expands to said predetermined circumference when said end is not in a stretched condition; and first and second stylus receptacles each having a closed end, an open end and a closed surface forming a cavity, wherein said first stylus receptacle is disposed on said tube adjacent said distal end and said second stylus receptacle is disposed on said proximal end, and wherein each receptacle is adapted to receive a positioning stylus that is inserted into said cavity for stretching said tubular body.

27. A surgical kit for shunting fluid in a fluid-carrying vessel, comprising:

a generally tubular shunt having a naturally biased configuration and at least one axially deformable configuration, comprising opposing larger circumference segments between opposing end portions, wherein each of said opposing larger circumference segments has an external circumference sufficient to prevent fluid from passing between said end portions and the inside wall of the vessel when said shunt is in said naturally biased condition; upper and lower wall portions defining a longitudinal axis, said upper wall portion having a recessed smaller-circumference segment disposed between said opposing larger circumference segments and having an internal circumference sufficient to maintain the natural fluid-flow volume in the vessel when said shunt is in said naturally biased configuration;

and a stylus receptacle integrally disposed on each of said opposing end portions; and at least one stylus configured to be operatively received in each of said stylus receptacles for transforming said shunt into said axially deformable configuration.

28. The surgical kit of claim 27 wherein exerting a selective force on at least one of said opposing larger circumference segments in an axial direction away from said smaller circumference segment, by means of said stylus operatively received in said respective receptacle, causes said external circumference of said larger circumference segments to selectively contract.

29. The surgical kit of claim 27 wherein said at least one stylus has a pre-formed shape optimally suited for accessing the vessel through a surgical incision.

30. The surgical kit of claim 27 wherein said at least one stylus is malleable.

31. The surgical kit of claim 27 wherein said larger circumference segments have tips configured for atraumatic insertion into a vessel.

32. A surgical kit for shunting fluid in a fluid-carrying vessel, comprising a generally tubular shunt having a naturally biased configuration and at least one axially deformable configuration, comprising
  a) first and second ends each having an external circumference sufficient to prevent fluid from passing between said end region and the inside wall of the vessel when said shunt is in said naturally biased configuration; and
  b) upper and lower wall portions defining a longitudinal axis of said shunt, said upper wall portion having a recessed central portion between said first and second ends and having an internal circumference sufficient to maintain the natural fluid flow volume in the vessel when said shunt is in said naturally biased, configuration and said lower wall portion extending substantially linearly along said longitudinal axis of said shunt;

first and second stylets each having a distal end and a proximal end, said distal end of said first stylet operatively attached to said first end of said shunt and said distal end of said second stylet operatively attached to said second end of said shunt; and a stylet positioning sleeve having a lumen configured for receiving said first or second stylet therethrough for stretching said tubular shunt.

* * * * *